United States Patent [19]
Arndt

[11] Patent Number: 6,086,529
[45] Date of Patent: Jul. 11, 2000

[54] BRONCHOSCOPIC MANIFOLD WITH COMPRESSIBLE DIAPHRAGMATIC VALVE FOR SIMULTANEOUS AIRWAY INSTRUMENTATION

[75] Inventor: George Arthur Arndt, Madison, Wis.

[73] Assignee: Wisconsin Medical, Inc., Madison, Wis.

[21] Appl. No.: 09/034,958

[22] Filed: Mar. 4, 1998

Related U.S. Application Data

[60] Provisional application No. 60/046,323, May 13, 1997.

[51] Int. Cl.$^7$ .............................. A61B 1/267; A62B 9/04
[52] U.S. Cl. ...................... 600/114; 600/120; 128/207.14
[58] Field of Search .................................. 600/114, 120; 128/204.18, 202.16, 207.14, 207.15, 207.16, 200.26, 912; 604/256, 167

[56] References Cited

U.S. PATENT DOCUMENTS

| | | | |
|---|---|---|---|
| 4,240,417 | 12/1980 | Holever | 128/207.15 |
| 4,351,328 | 9/1982 | Bodai . | |
| 4,580,556 | 4/1986 | Kondur | 600/120 |
| 4,715,360 | 12/1987 | Akui et al. | 128/912 |
| 4,819,664 | 4/1989 | Nazari | 128/207.15 |
| 4,836,199 | 6/1989 | Palmer . | |
| 4,848,331 | 7/1989 | Northway-Meyer | 128/207.14 |
| 5,000,745 | 3/1991 | Guest et al. | 604/256 |
| 5,167,636 | 12/1992 | Clement | 604/167 |
| 5,176,652 | 1/1993 | Littrell | 604/167 |
| 5,181,508 | 1/1993 | Poole, Jr. | 128/207.14 |
| 5,197,463 | 3/1993 | Jeshuran | 128/207.14 |
| 5,329,921 | 7/1994 | Socaris et al. | 128/207.14 |
| 5,333,607 | 8/1994 | Kee . | |
| 5,598,840 | 2/1997 | Iund et al. | 128/207.14 |
| 5,628,306 | 5/1997 | Kee et al. . | |
| 5,735,271 | 4/1998 | Lorenzen et al. | 128/207.14 |
| 5,746,199 | 5/1998 | Bayron et al. | 128/207.16 |
| 5,762,063 | 6/1998 | Coates et al. | 128/207.16 |
| 5,904,648 | 5/1999 | Arndt et al. . | |

OTHER PUBLICATIONS

Arndt GA et al., "Co–axial placement of an endobronchial blocker," Can J Anesth 41: 1126–1127, 1993.

Ginsberg RJ., "New technique for one–lung anesthesia using an endobronchial blocker," J Thorac Cardiovasc Surj 82:595–596,1981.

MacGillivary RG., "Evaluation of a new tracheal tube with a moveable bronchus blocker," Anaesthesia 43: 687–689, 1988.

Larson CE, Gasior TA., A device for endobronchial blocker placement during one–lung anesthesia.Anesth&Analg71:311–2,1990.

*Primary Examiner*—John P. Leubecker
*Attorney, Agent, or Firm*—Quarles & Brady LLP

[57] ABSTRACT

An apparatus and method for accomplishing simultaneous bronchoscopy and airway instrumentation and securing the instrument in place using an adjustable threaded gastight seal. The apparatus consisting of a hollow elongated manifold for simultaneous fiberoptic bronchoscopy through a fiberoptic port (4) and introduction a secondary tubular instrument (2) through a threaded secondary instrument port (5) while maintaining mechanical ventilation of a intubated patient using a ventilation port (7) and endotracheal tube connection port (6). The secondary instrument port (5) is constructed in a manner to allow introduction of a tubular instrument into the airway and form an adjustable gastight seal. It consists of a compressible perforated diaphragmatic seal (17) sandwiched between a threaded secondary instrument port and threaded perforated secondary instrument cap (18) so that the threaded cap may be torqued into the threaded secondary port (5) compressing the compressible diaphragmatic seal (17) against the inserted secondary instrument (2) forming airtight adjustable seal and affixing the secondary instrument in place. In addition, the secondary instrument port (5) allows chronic instrumentation following the removal of the fiberoptic bronchoscope (3) or reinspection.

14 Claims, 2 Drawing Sheets

6,086,529

BRONCHOSCOPIC MANIFOLD WITH COMPRESSIBLE DIAPHRAGMATIC VALVE FOR SIMULTANEOUS AIRWAY INSTRUMENTATION

CROSS-REFERENCE TO RELATED COPENDING APPLICATIONS

This application claims priority of provisional application Ser. No. 60/046,323, filed on May 13, 1997.

FIELD OF THE INVENTION

The present invention relates generally to the simultaneous fiberoptic bronchoscopy and instrumentation of the airway and lungs of medical or surgical patients, and more particularly, to novel valve mechanism by with which a catheter can be placed in the lung or airway under direct fiberoptic guidance and then be affixed into position forming a gas tight seal with a compressible diaphragmatic seal where the compression is variable using a threaded compression mechanism.

BACKGROUND OF THE INVENTION

Medical and surgical patients are commonly intubated or have a tube installed into their trachea to allow mechanical ventilation. In these patients, it is sometimes required in their medical management to install a second catheter through the endotracheal tube for some specific purpose. These second catheters may be placed for monitoring or therapy. Parameters which may be monitored may be gas composition, pressure or temperature. Therapy which may be delivered may include jet ventilation, the placement of a balloon tipped catheter to obstruct a portion of the airway or any other therapy which be delivered using a second catheter installed through an endotracheal tube. These catheters may lie past the end of the endotracheal tube and should be positioned and inspected through the endotracheal tube with a flexible fiberoptic bronchoscope, a flexible fiberoptic instrument. Both the fiberoptic bronchoscope and the second catheter will need to be installed through a manifold capable of allowing simultaneous ventilation, fiberoptic bronhoscopy, and airway instrumentation. The manifold must be capable of forming a gastight seal following introduction and removal of the fiberoptic bronchoscope. The manifold must also have a sealing mechanism to allow the second catheter to be positioned, be affixed in place, and reform a gastight seal if pulmonary physiology changes causing gas leakage past the seal from higher ventilation pressures.

The most relevant, known ventilating instrumentation prior art patent is U.S. Pat. No. 4,351,328. In this patent by Bodai, a manifold is provided for airway insertion of an instrument, most commonly, a fiberoptic bronchoscope, while maintaining mechanical ventilation of either a medical or surgical patient. Difficulty has been encountered when in placing two instruments simultaneously into the airway. Often the technique required by the prior art requires two manifolds placed in series making the procedure cumbersome, time consuming, and traumatic for the patient. The prior art valve mechanism does not allow an instrument to be fixed in place or form a reliable airtight seal necessary for long periods, several hours of instrumentation.

In U.S. Pat. Nos. 5,333,607 and 5,628,306 Kee describes a ventilator manifold with an accessory port for the introduction of a catheter tube into the endotracheal tube of an intubated patient. This manifold incorporates an accessory port with a valve normally held in the closed position. The accessory port is opened with the attachment of an accessory device to open the valve and allow introduction of the catheter tube. This device does not allow the compressive force of the enclosed diaphragmatic valve to be varied against the outer wall of the inserted catheter tube. The device also requires the use of an accessory device to open the valve which in clinical practice is cumbersome requiring the presence of the accessory device or a special catheter tube incorporating the accessory device into its construction.

The literature describes common medical procedures requiring simultaneous fiberoptic bronchoscopy and airway instrumentation with a catheter tube and disclose the difficulty of simultaneous instrumentation and bronchoscopy of the airway.

The prior art describes a manifold to allow instrumentation of a medical or surgical patient's airway while being mechanically ventilated using an endotracheal tube previously placed in the patient's trachea. However, the prior art does not allow simultaneous fiberoptic bronchoscopy and airway instrumentation with a second instrument being tubular in shape. The prior art has a number of disadvantages.

a) The manifold does include an accessory port for the introduction of a second instrument following introduction of a fiberoptic bronchoscope.

b) The instrumentation port seals do not form an airtight seal following the placement of a second instrument. This allows leakage of ventilation gases and possible patient harm.

c) The instrument port seals are not adjustable in the amount of compression exerted on the instrument. Compression may need to be adjusted to prevent instrument damage or to stop a leakage of ventilating gases if pulmonary physiology changes requiring a higher ventilation pressure from a mechanical ventilator.

d) The instrumentation port does not allow the instrument to be affixed in position after correct positioning using a fiberoptic bronchoscope.

BRIEF SUMMARY OF OBJECTS AND ADVANTAGES OF THE PRESENT INVENTION

In brief summary, the present invention is intended to overcome the aforementioned limitations of the prior art and comprises a novel manifold to allow continuous mechanical ventilation of medical and surgical patients while allowing simultaneous fiberoptic bronchoscopy and instrumentation with a second tubular instrument with the instrumentation manifold port having a novel sealing mechanism which is adjustable in compression, forms an airtight seal and can affix the second instrument in place after correct positioning using a fiberoptic bronchoscope. In its present preferred configuration, the second instrument may be left in place several hours after removal of the fiberoptic bronchoscope.

Accordingly, besides the objective and advantages of the described manifold, several objectives and advantages are:

a) to provide a manifold with a minimum of four ports for mechanical ventilation, connection to an endotracheal tube, fiberoptic bronchoscopy, and secondary simultaneous instrumentation.

b) to provide a secondary instrumentation port constructed of a threaded port with a threaded open ended cap with a deformable perforated elastic diaphragm between the port and cap.

c) to provide variable tension or compression on the outer surface a secondary tubular instrument inserted through the secondary instrumentation port by screwing or torquing the cap so as to compress the diaphragm between the threaded port and cap.

d) to provide a means of stopping the loss of ventilatory gases during mechanical ventilation through the instrumentation port during chronic instrumentation by torquing the end cap to increase the tension or compression of the diaphragm around the outer wall of the secondary instrument.

e) to provide a means of affixing the secondary tubular instrument in position in relation to the manifold, endotracheal tube and patient airway after correct positioning using a fiberoptic bronchoscopy by torquing the end cap to compress the tubular secondary instrument and deformable perforated elastic diaphragm against each other affixing the secondary instrument in place.

f) to provide a secondary instrumentation port oriented at an angle in relation to the bronchoscopy port to provide optimal introduction of the secondary tubular instrument into the body of the manifold.

SUMMARY

This and additional objects are accomplished by the present invention to allow a patient being mechanically ventilated with an installed endotracheal tube to undergo simultaneous fiberoptic bronchoscopy and instrumentation with a second tubular instrument using a novel and unique manifold. The manifold port of the secondary instrument incorporates a threaded port accepting a threaded cap with a hole to allow a perforated diaphragm to be compressed between the threaded manifold port and end cap compressing the perforated diaphragm against the secondary instrument. The compression of the diaphragm against the secondary instrument is variable to allow the secondary instrument to positioned and moved yet form an airtight seal affixing the secondary instrument in place in relation to the patient airway after correct positioning with a fiberoptic bronchoscope. The secondary instrument may be left in place for several hours after the fiberoptic bronchoscope has been removed and the fiberoptic port end cap closed. Leakage of ventilatory gases may be stopped by torquing the end cap against the diaphragm increasing the compression against the wall of the secondary instrument as when the pathophysiology of a patient lung may require a higher ventilating pressure from a ventilator.

DESCRIPTION OF INVENTION

Figure 2:
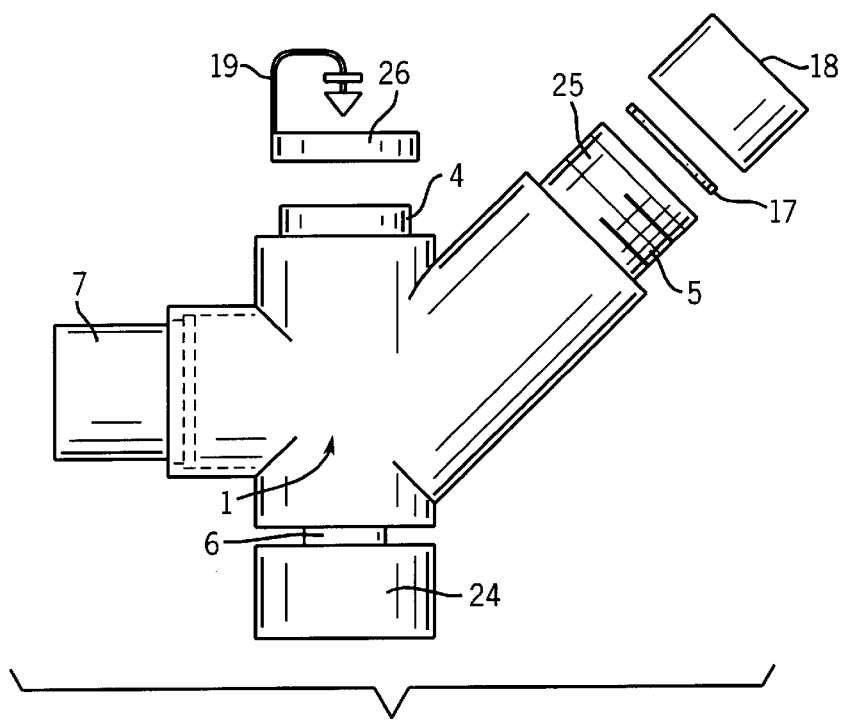
FIG. 2 is a perspective representation of the manifold apparatus embodying the present invention

FIG. 2 generally illustrates a bronchoscopic manifold with compressible diaphragmatic valve for simultaneous airway instrumentation consisting of a hollow manifold with four ports, a port being a tubular passage opening to the hollow body of the manifold consisting of a tubular conduit open to the manifold and exterior to the manifold.

A mechanical ventilation port (7) opens to the manifold interior and allows connection to a mechanical ventilator (9) through commercially available mechanical ventilator connection tubing (8). An endotracheal tube connection port (6) opens to the manifold interior and is located in an orthogonal position to the mechanical ventilation port (7) connects to an endotracheal tube port attachment collar (24). The endotracheal tube port attachment collar (24) allows connection of the bronchoscopic manifold with compressible diaphragmatic valve for simultaneous airway instrumentation to an endotracheal tube (10). The endotracheal tube attachment collar, allows the manifold (1) to rotate along freely the central axis or be fixed along the central axis. A bronchoscopic manifold port (4) is located opposite and in line along the central axis to the endotracheal tube connection port (6) and open to the interior of the manifold (1). The external opening of the bronchoscopic manifold port (4) is covered by a commercially available bronchoscopic end cap with attached sealing lid (26) which may be opened and closed to allow the introduction and removal of a fiberoptic bronchoscope (3) and form a gas tight seal when closed. A secondary instrument port (5) is located at an angle of 15 to 70 degrees in relation to the central axis of the manifold and the bronchoscopic manifold port (4) to allow easy introduction of a secondary tubular instrument (2) into the manifold and open to the interior of the manifold. The secondary instrument port (5) is threaded with a set of external threads (25). The secondary instrument port accepts an internally threaded secondary instrument cap (18) with a secondary instrument cap end hole with the male and female threads of each being the same pitch. Between the threaded port (5) and the end cap (18) is a compressible diaphragmatic seal (17) of similar diameter to the outer diameter of the threaded secondary instrument port (5). The compressible diaphragmatic seal is made of a deformable plastic or rubber or elastomeric material such as latex, polyurethane, silicone rubber, or silicone plastic.

Operation of Invention

Figure 1:
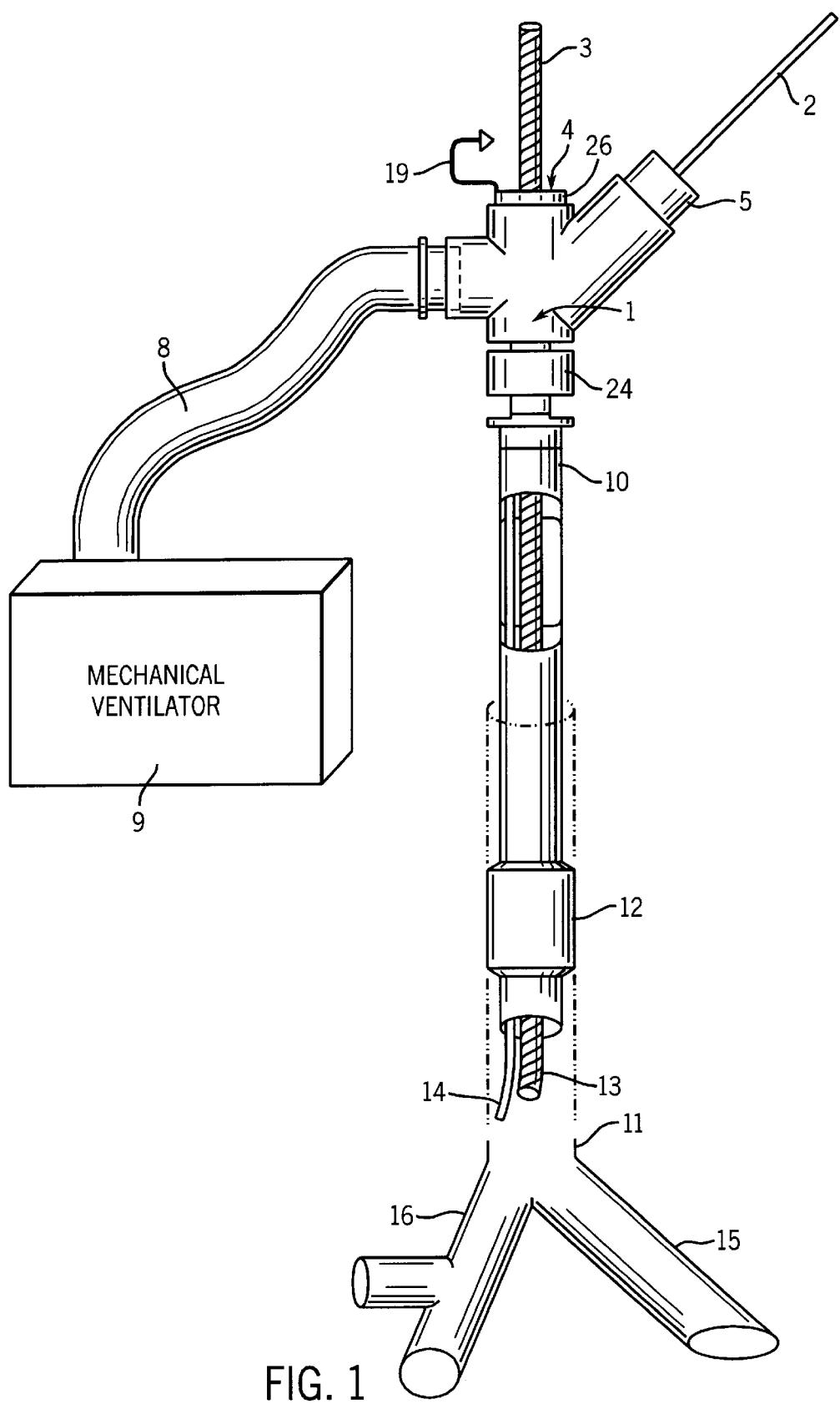
FIG. 1 generally illustrates the use of the improved manifold to allow simultaneous fiberoptic bronchoscopy and secondary instrumentation of a patient who is being mechanically ventilated.
Figure 3:
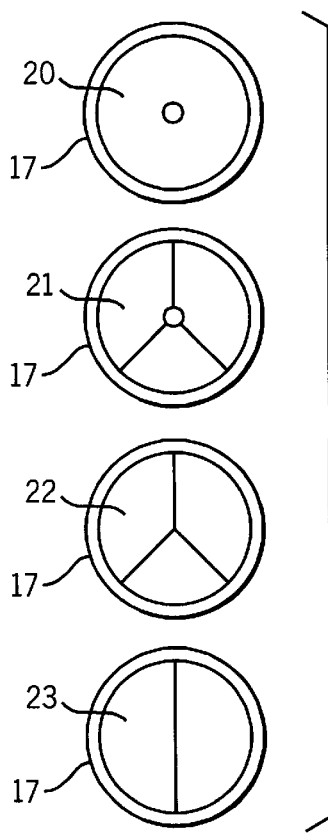
FIG. 3 is various perspective views of different type of compressible diaphragm membranes for use in the secondary instrumentation port.

Referring initially to FIG. 1, the most common type of connection to a mechanical ventilator is shown. The distal trachea is shown. The remaining patient is not depicted and is not relevant. Within the trachea (11) is installed, a commercially available endotracheal tube assembly (10) in which both ends are open. The endotracheal tube (10) is positioned in the trachea (11) to lie above the bifurcation of the trachea into a right main stem bronchus (16) and left mainstem bronchus (15). The endotracheal tube assembly is connected to a bronchoscopic manifold with compressible diaphragmatic valve for simultaneous airway instrumentation (1) through an endotracheal tube port attachment collar (24). A fiberoptic bronchoscope (3) is inserted through the bronchoscopic manifold port (4) and advanced to be in the trachea. A secondary tubular instrument (2) has been advanced through the threaded secondary instrument port (5). A secondary instrument is a commercially available tubular catheter device which may perform various tasks in the distal trachea. The secondary instrument may be an endobronchial blocker, a fiberoptic bundle, a small electronic instrument placed in the distal end of a catheter, a jet ventilation catheter or any device which may be placed with a small tubular conduit so as the internal diameter of the endotracheal tube (10) and trachea is large enough to accept both the fiberoptic bronchoscope and secondary instrument (2). The secondary instrument (2) may be positioned using the distal end of the fiberoptic bronchoscope (13) to lie in an exact position in the trachea (11). The fiberoptic bronchoscope (3) may be removed after the secondary instrument (2) has been correctly positioned and the bronchoscopic manifold port (4) sealed with the bronchoscopic end cap seal (19). The secondary instrument (2) may be affixed into position and an airtight seal formed by torquing the threaded secondary instrument cap (18) into the threaded secondary instrument port (5) compressing the compressible diaphragmatic seal (17) against the outer walls of the secondary instrument (2). The compressible diaphragmatic seal (17) is compressed between the threaded end cap (18) and the threaded port (5) by torquing the threaded end cap (18) into closer approximation to the threaded port. The compressible diaphragm seal (17) is thereby compressed and deformed forming an airtight seal with a secondary instrument (2) and locking it in place. The compressive force on the diaphragm (17) may be altered by torquing or untorquing the end cap (18). The compressive forces is thereby precisely adjustable allowing the secondary instrument (2) to be easily moved or positioned within the instrument port (5) by untorquing the end cap (18) or form a gas tight seal affixing the secondary instrument (2) in place by torquing the end cap (18) into the instrument port (5). FIG. 3 illustrates different openings in the compressible diaphragmatic seal to alter the mechanical properties of the seal during compression. A diaphragmatic seal with a single hole (20) is shown. A diaphragmatic seal with a single hole and radial slits (21) is shown. A diaphragmatic seal with radial slits and no central hole (22) is shown. A diaphragmatic slit with a single slit (23) is shown.

Conclusion, Ramification and Scope of the Invention

Accordingly, the reader will see that the manifold for ventilation of medical and surgical patients of this invention can be used to allow simultaneous fiberoptic bronchoscopy and the introduction of a secondary tubular instrument into the trachea of intubated patient and affix the tubular secondary instrument in place forming a gastight seal using a torquable diaphragmatic seal. The manifold incorporates a minimum of four ports for connection of a mechanical ventilator to an endotracheal tube to allow fiberoptic bronchoscopy, and simultaneous airway instrumentation. Each port is designed to perform specific tasks and oriented in position to allow simultaneous ventilation, fiberoptic bronchoscopy and introduction and placement of a secondary tubular instrument under direct vision. In addition, the instrumentation port is designed with a perforated diaphragmatic seal in which the compressive force against the wall of the secondary instrument is adjustable by compressing the diaphragmatic seal between the threaded secondary instrumentation port and the threaded secondary instrumentation cap with an end hole so as to form a gas tight seal against a secondary tubular instrument placed through the instrument port and affix it in position. The secondary instrument port is oriented at an angle of 15 degrees to 70 degrees in relation to the bronchoscopy port to allow easy and timely introduction of the secondary tubular instrument into the body of the manifold. Furthermore, the manifold has the additional advantage in that it allows placement of a secondary tubular for long periods of time without movement by being locked into position by the sealing mechanism of the secondary instrument port.

It allows easy inspection of the secondary instrument after primary placement with a fiberoptic bronchoscope by reintroduction of the fiberoptic bronchoscope through the sealable bronchoscopy port.

It allows the secondary instrument seal to compensate for changes in pulmonary physiology following secondary instrument airway introduction when higher ventilatory pressure are required causing the leaking of ventilatory gases past the seal. This is accomplished by torquing the threaded end cap into the threaded port compressing the compressible diaphragmatic seal against the secondary instrument reforming a gastight seal.

It incorporates a diaphragmatic seal whose mechanical compressive properties may be altered by changing the shape of the perforation.

Although the description above contains many specificities, these should not be construed as limiting the scope of the present invention but merely providing illustration of some of the presently preferred embodiment of this invention. For example, the manifold could have additional ports added for the sampling of respiratory gases, monitoring of airway pressure during ventilation, or the introduction of a third instrument.

Thus, the scope of the invention should be determined by the appended claims and the legal equivalent rather than by the example given.

What is claimed:

1. An airway manifold comprising:
    an elongated hollow body having proximal and distal ends and an interior passageway having a long axis and opening to at least four ports;
    a first port open to the proximal end of the interior passageway along the long axis of the hollow body;
    a second port open to the distal end of the interior passageway along the long axis of the hollow body and accommodating a resealable gas-tight cover;
    a third port open to the interior passageway;
    a fourth port open at one end directly to the interior passageway and disposed opposite the third port, the fourth port oriented at an angle of about 15 degrees to 70 degrees from the long axis relative to distal end of the hollow body, the fourth port accommodating a perforated compressible diaphram for releasably securing a catheter device in the fourth port.

2. The airway manifold according to claim 1 wherein the diaphragm is variably compressible.

3. The airway manifold according to claim 1 wherein the diaphragm comprises a deformable material.

4. The airway manifold according to claim 1 wherein the diaphragm defines a single central hole.

5. The airway manifold according to claim 1 wherein the diaphragm defines a single central hole and more radial slits extending from the central hole to an edge of the diaphragm.

6. The airway manifold according to claim 1 wherein the diaphragm defines at least one radial slit extending from a center to an edge of the diaphragm.

7. The airway manifold according to claim 1 wherein the diaphragm defines one slit.

8. The airway manifold according to claim 1 wherein the manifold further comprises an end cap on the fourth port, the compressible perforated diaphragm being sandwiched between the end cap and the fourth port.

9. The airway manifold according to claim 1 further comprising a catheter device traversing the fourth port.

10. A multiport airway manifold for connection to an endotracheal tube, the manifold comprising:
    an elongated hollow body having proximal and distal ends and an interior passageway having a long axis;
    an endotracheal tube connection port open to the proximal end of the interior passageway along the axis of the hollow body;
    a bronchoscopy port open to the distal end of the interior passageway along the axis of the hollow body;
    a resealable gas-tight cover on the bronchoscopy port adapted for removable insertion of a bronchoscope into the bronchoscopy port and through the hollow body;
    a mechanical ventilation port open to the interior passageway and adapted for connection to a mechanical ventilator;

an instrument port open at one end directly to the interior passageway and disposed opposite the mechanical ventilation port, the instruction port oriented at an angle of about 15 degrees to 70 degrees from the long axis relative to the distal end of the hollow body, the instrument port accommodating a perforated compressible diaphragm for releasably securing a catheter device in the instrument port.

11. A method for selectively introducing a catheter device into a ventilated lung of a patient having an endotracheal tube open at two ends and positioned above a bifurcated trachea, the method comprising the steps of:

providing a catheter device and an airway manifold that comprises an elongated hollow body having proximal and distal ends and an interior passageway having a long axis, a first port open to the proximal end of the interior passageway along the axis of the hollow body, a releasably sealable gas-tight second port open to the distal end of the interior passageway along the axis of the hollow body, a third port open to the interior passageway, a fourth port open at one end directly to the interior of the interior passageway and oriented at an angle of about 15 degrees to 70 degrees from the long axis relative to the distal end of the hollow body, the fourth port being adapted for releasably securing the catheter device in the fourth port, the catheter device traversing the fourth port;

attaching the endotracheal tube to the first port;

attaching a ventilator to the third port;

guiding a fiberoptic endoscope through the second port, through the interior passageway, through the endotracheal tube and into the trachea;

guiding the catheter device through the interior passageway, through the endotracheal tube and into the trachea; and securing the catheter device in the fourth port.

12. A method as in claim 11 wherein the catheter device is selected from the group consisting of an endobronchial blocker, a fiberoptic bundle, and a jet ventilation catheter.

13. A method as in claim 11 wherein the catheter device is an endobronchial blocker and the catheter device is guided into a mainstem bronchus.

14. A method as in claim 11 wherein the instrument is a bronchoscope.

* * * * *